(12) United States Patent
Vilenchik et al.

(10) Patent No.: US 9,156,879 B1
(45) Date of Patent: Oct. 13, 2015

(54) CHROMATOGRAPHY MEDIA

(75) Inventors: Lev Z. Vilenchik, Waltham, MA (US); Krishna Kalghatgi, Westboro, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 254 days.

(21) Appl. No.: 13/285,433

(22) Filed: Oct. 31, 2011

Related U.S. Application Data

(60) Provisional application No. 61/408,292, filed on Oct. 29, 2010.

(51) Int. Cl.
| | |
|---|---|
| *C07K 1/00* | (2006.01) |
| *C07K 1/14* | (2006.01) |
| *C07K 1/16* | (2006.01) |
| *B01J 20/24* | (2006.01) |
| *B01J 20/26* | (2006.01) |
| *C07K 1/22* | (2006.01) |
| *B01J 20/00* | (2006.01) |
| *B01J 20/22* | (2006.01) |
| *B01J 20/281* | (2006.01) |
| *B01J 20/282* | (2006.01) |
| *B01J 20/283* | (2006.01) |
| *B01J 20/285* | (2006.01) |

(52) U.S. Cl.
CPC . *C07K 1/16* (2013.01); *B01J 20/00* (2013.01); *B01J 20/22* (2013.01); *B01J 20/24* (2013.01); *B01J 20/26* (2013.01); *B01J 20/261* (2013.01); *B01J 20/281* (2013.01); *B01J 20/282* (2013.01); *B01J 20/283* (2013.01); *B01J 20/285* (2013.01); *C07K 1/14* (2013.01); *C07K 1/22* (2013.01)

(58) Field of Classification Search
CPC ...... C07K 14/76; C07K 14/765; C07K 17/00; C07K 17/14; C07K 1/14; C07K 1/16; C07K 1/22; B01D 14/362; B01D 15/3804; B01J 20/00; B01J 20/24; B01J 20/26; B01J 20/261; B01J 20/28054; B01J 20/28078; B01J 200/00; B01J 20/22; B01J 20/281; B01J 20/282; B01J 20/283; B01J 20/285
See application file for complete search history.

(56) References Cited

U.S. PATENT DOCUMENTS

| | | | |
|---|---|---|---|
| 7,731,844 B2 * | 6/2010 | Mallet et al. | 210/198.2 |
| 2005/0090652 A1 * | 4/2005 | Bertucci et al. | 530/417 |
| 2010/0055667 A1 | 3/2010 | Hage et al. | |

FOREIGN PATENT DOCUMENTS

| | | | | |
|---|---|---|---|---|
| WO | WO 2009/141384 | * | 11/2009 | C12N 9/64 |

OTHER PUBLICATIONS

Rupert, Journal of Chromatography (1983) 266, 23-37.*
Kim et al., Journal of Chromatography A (2004) 1049, 51-61.*
Swiderek et al., Techniques in Protein Chemistry VI (1995) Academic Press, 267-275.*
Vlasák et al. (Journal of Polymer Science: Polymer Symposium (1979) 66, 59-64).*
Kuhn et al., The Journal of Biological Chemistry (1975) 250(11), 4220-4228.*
Cassiano NM, Barreiro JC, Moraes MC, Oliveira RV, Cass QB. Restricted-access media supports for direct high-throughput analysis of biological fluid samples: review of recent applications. Bioanalysis. Jun. 2009;1(3):577-94.
Papp R, Mullett WM, Kwong E. A method for the direct analysis of drug compounds in plasma using a single restricted access material (RAM) column. J Pharm Biomed Anal. Nov. 15, 2004;36(3):457-64.
Haruyo Sanbe and Jun Haginaka. Restricted access media-molecularly imprinted polymer for propranolol and its application to direct injection analysis of (β-blockers in biological fluids. Analyst, 2003,128, 593-597.
Yamamoto E, Kato T, Mano N, Asakawa N. Effective on-line extraction of drugs from plasma using a restricted-access media column in column-switching HPLC equipped with a dilution system: application to the simultaneous determination of ER-118585 and its metabolites in canine plasma. J Pharm Biomed Anal. Jul. 12, 2009;49(5):1250-5. Epub Mar. 4, 2009.

* cited by examiner

*Primary Examiner* — Karlheinz R Skowronek
*Assistant Examiner* — Catherine Mader

(57) ABSTRACT

The present invention provides, in part, a chromatographic restricted access media comprising aminopropyl groups derivatized with polysuccinamide that is derivatized with 1-ethylpropylamine and denatured human serum albumin. Methods of purifying polypeptides and complexes thereof are also provided.

15 Claims, 9 Drawing Sheets

CHROMATOGRAPHY MEDIA

The present application claims the benefit of U.S. provisional patent application No. 61/408,292 filed on Oct. 29, 2010 which is herein incorporated by reference in its entirety.

FIELD OF THE INVENTION

The field of the invention relates to a restricted access media for chromatographic purification and methods of use thereof.

BACKGROUND OF THE INVENTION

Two classes of chromatography are adsorption chromatography (AC) and size exclusion chromatography (SEC). Reverse and normal phase chromatography, ion exchange chromatography, chiral chromatography are in the class of AC. Separation here is due to different energetic interactions between molecules of the substance undergoing to the chromatographic separation. Another class includes SEC that separates substances according to molecular size (other parameters affecting separation include size of pores in the media, size of the chromatographic column, flow rate, temperature, injection volume and sensitivity of used detector). Separation, using SEC, between molecules having a size difference of at least two fold is usually sufficient. Drug screening frequently requires the separation of protein-ligand complexes from non-bound ligand molecules. The complex may then need to be analyzed. If, however, short or small columns are in use, the SEC separation may be poor. If needed, additional resolution may be affected by adsorption between small molecules and the inner surface of pores of the SEC media. Generally, the interaction increases retention of the small molecules and has no effect on large molecules like proteins if they are not able to penetrate inside the pores. This variety of media is known as "restrictive access media" or RAM. Performance of the RAM is dependable on its design. As a result of using this media, complete and fast separation of protein-ligand complexes and low molecular weight compounds is achieved Known RAM are generally not able to separate protein-ligand complexes from detergents that solubilize proteins such as membrane proteins. Frequently, the required detergent concentration results in formation of micelles comparable in size to the target protein. Existing media do not allow SEC based separation of the micelles from protein-ligand complexes. This drawback causes problems with characterizing the protein-ligand complexes, for example, using liquid chromatography-mass spectroscopy (LC-MS) screening, detergent molecules come into the mass spectrometer (MS) together with the ligands initially bound to target. The detergent molecules then suppress the ligand ionization.

SUMMARY OF THE INVENTION

The present invention provides a chromatography resin designed to disperse detergent micelles, effect separation of the individual detergent molecules from target ligand complex, and prevent their interference with MS.

The present invention provides a particle (e.g., a silica particle, for example, a silica gel) comprising a diameter of about 5 microns and pores of about 60 angstroms in diameter; wherein the surface of the particle pores is derivatized with aminopropyl groups that are coated with polysuccinamide polymers which polymers are coated with 1-ethylpropylamine and with denatured human serum albumin. Any particle that is derivatized with 1-ethylpropyl amidated polysuccinamide and coated with human serum albumin; that is produced by a process comprising: (1) incubating a support particle comprising aminopropyl groups (e.g., a silica gel particle comprising aminopropyl groups) with 1% polysuccinamide in dimethylformamide; (2) incubating the particle with denatured human serum albumin; and (3) incubating the particle with 1-ethylpropylamine; forms part of the present invention. For example, the present invention includes any particle produced by a process comprising (1) incubating a support particle comprising aminopropyl groups (e.g., silica gel particle comprising aminopropyl groups) with 1% polysuccinamide in dimethylformamide at about 50° C.; and then washing the particle to remove excess polysuccinamide; (2) incubating the particle with a mixture of dimethylformamide and denatured human serum albumin at about 50° C.; and then washing the particle to remove excess denatured human serum albumin; (3) incubating the particle with 1-ethylpropyl amine in dimethylformamide at about 50° C., then washing the particle to remove excess 1-ethylpropylamine; wherein said particle has a diameter of about 5 microns and pores with a diameter of about 60 angstroms—for example, wherein the process is performed in the order indicated: step 1, then step 2, then step 3. In an embodiment of the invention, such particles comprise about 100% of said aminopropyl groups are derivatized with polysuccinamide; about 100% of said polysuccinamidyl groups are derivatized with human serum albumin and 1-ethylpropylamine. In an embodiment of the invention, said wash step in (1) comprises washing with particle with dimethylformamide and a with mixture of dimethylformamide and water; and/or said wash step in (2) comprises washing with particle with a mixture of dimethylformamide and water and with water; and/or said wash in step (3) comprises washing with particle with dimethylformamide, with water and with an alcohol such as ethanol or methanol.

The present invention also provides a method for purifying a polypeptide or complex thereof or for dispersing detergent micelles (e.g., wherein the detergent is sodium dodecyl sulfate, Cholate, Deoxycholate, C16TAB, LysoPC, CHAPS, Zwittergent 3-14, Octylglucoside, Digitonin, C12E8, Lubrol, Triton X-100, Nonidet P-40 or Tween 80) from a sample comprising a polypeptide or complex thereof comprising adding the sample to a column comprising any of the particles set forth herein and collecting eluate comprising the polypeptide or complex thereof. Such a method may further include additional purification steps performed before or after use of such particles, for example, purifying said polypeptide by size exclusion chromatography, anion exchange chromatography, cation exchange chromatography, hydrophobic interaction chromatography, hydroxyapatite chromatography, filtration, diafiltration, ultrafiltration, precipitation or viral filtration.

The present invention also provides a method for making a particle that is derivatized with 1-ethylpropyl amidated polysuccinamide and coated with human serum albumin; comprising: (1) incubating a support particle comprising aminopropyl groups (e.g., silica gel particle comprising aminopropyl groups) with 1% polysuccinamide in dimethylformamide; (2) incubating the particle with denatured human serum albumin; and (3) incubating the particle with 1-ethylpropylamine. For example, in an embodiment of the invention, the method comprises (1) incubating a support particle comprising aminopropyl groups with 1% polysuccinamide in dimethylformamide at about 50° C.; and then washing the particle to remove excess polysuccinamide; (2) incubating the particle with a mixture of dimethylformamide and denatured human serum albumin at about 50° C.; and then washing the particle to remove excess denatured human serum albumin; and (3) incubating the particle with 1-ethylpropyl amine in dimethylformamide at about 50° C., then washing the particle to remove excess 1-ethylpropylamine; wherein said particle has a diameter of about 5 microns and pores with a diameter of about 60 angstroms;—for example, wherein the method is performed in the order indicated: step 1, then step 2, then step 3. In an embodiment of the invention, the wash in step (1) comprises washing with particle with dimethylformamide and a with mixture of dimethylformamide and water; the wash in step (2) comprises washing with particle with a mixture of dimethylformamide and water and with water; and the wash in step (3) comprises washing with particle with dimethylformamide, with water and with an alcohol such as ethanol or methanol.

DETAILED DESCRIPTION OF THE INVENTION

Figure 4:
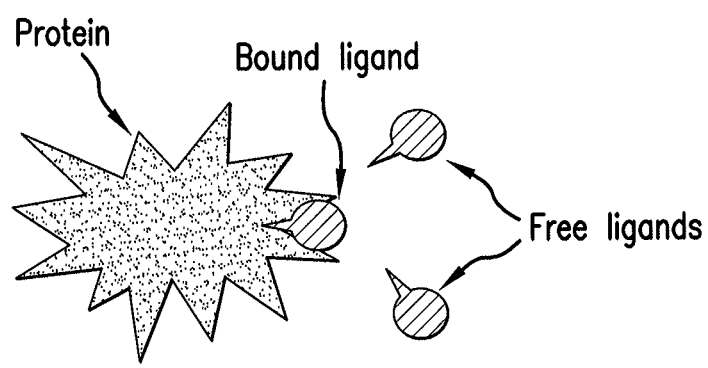
FIG. 4: Schematically shows the components of a mixture resulting from the generation of a protein-ligand complex. Complexed molecules (protein with ligand) and free ligand molecules are present. Such molecular species can be resolved using the RAM of the present invention.
Figure 5:
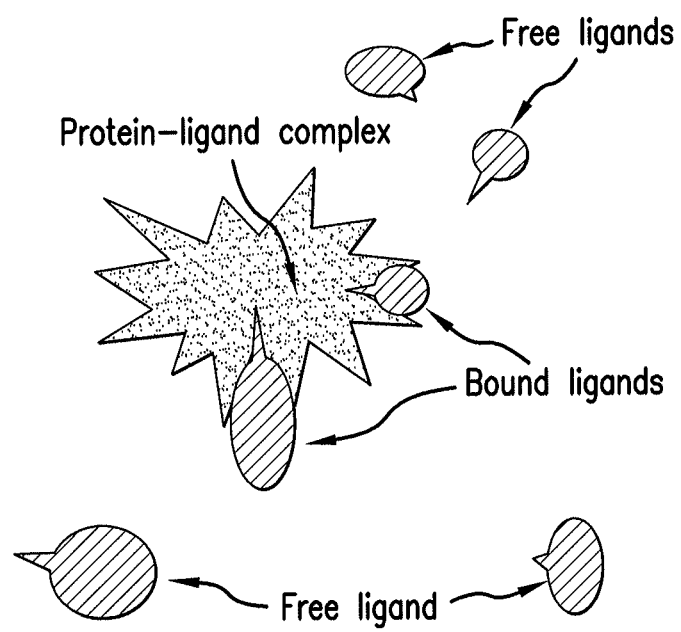
FIG. 5: Schematically shows the components of a mixture resulting from the generation of a protein-multiligand complex. Complexed molecules (protein with more than one ligand) and free ligand molecules are present. Such molecular species can be resolved using the RAM of the present invention.

The present invention provides, in an embodiment of the invention, a drug screening restrictive access media based on derivatized silica gel. The media allows complete separation small ligand molecules from large protein-ligand complex molecules quickly, e.g., between 10-20 seconds, and the media also efficiently disperses detergent micelles to prevent complication of mass spectrometric analysis of the final protein preparation due to detergent molecules. See, for example, the diagrams in FIGS. 4 and 5.

Figure 9:
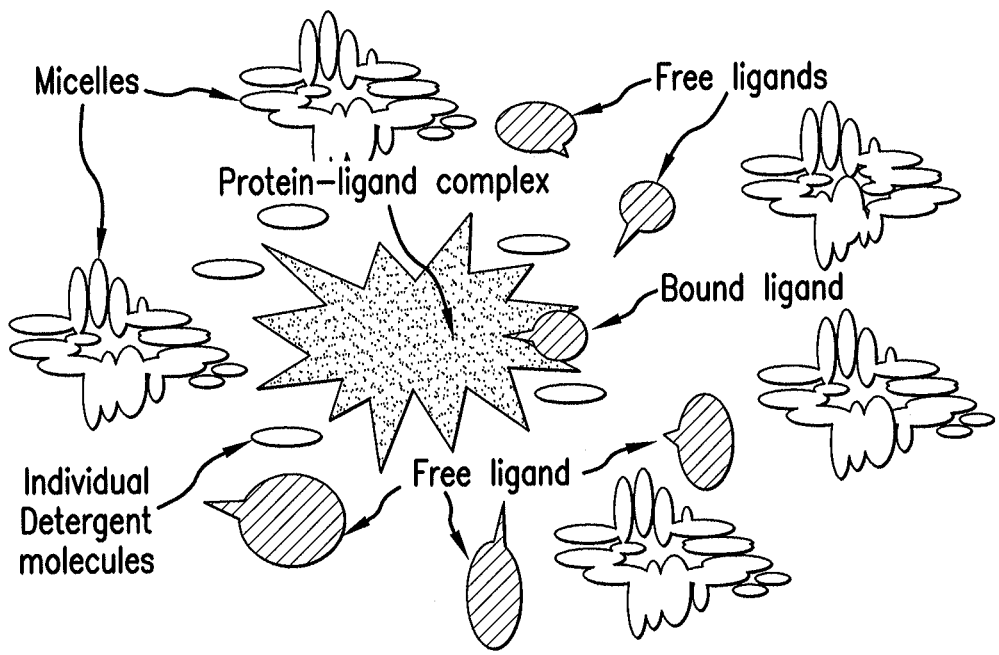
FIG. 9: schematically shows a reaction mixture of membrane protein and ligands in the presence detergent micelles. The interaction of the various components in the mixture with the RAM of the present invention are indicated.

Detergent contamination is particularly problematic for mass spectroscopic analysis of solubilized proteins. Interfering effects of detergent contamination include background ions that obscure the protein signal, suppression of the sample signal, and adduct formation. See for example, FIG. 9 illustrating the components in a composition comprising a detergent-solubilized protein complexed with ligand molecules. The present invention is particular effective at removing detergent micelles from protein-ligand complexes.

"Detergent micelles" are aggregates of detergent monomers wherein the nonpolar ends of the monomers are sequestered inward, avoiding exposure to water (in an aqueous environment), and the polar ends are oriented outward in contact with the water. During detergent cell lysis, the detergents penetrate between the cellular membrane bilayers at concentrations sufficient to form mixed micelles with, e.g., phospholipids and membrane proteins. Both the number of detergent monomers per micelle (aggregation number) and the range of detergent concentration above which micelles form (called the critical micelle concentration, CMC) are properties specific to each particular detergent. The CMC is the concentration of a detergent above which micelles are spontaneously formed. Removal of detergent micelles from a system, e.g., by use of the RAM of the present invention, will decrease the micelle concentration around the protein molecules and, thus, improve ligand purity and detection, e.g., by mass spectroscopy.

Examples of detergents include, but are not limited to SDS, Cholate, Deoxycholate, C16TAB, LysoPC, CHAPS (3[(3-cholamidopropyl)dimethylammonio]-1-propanesulfonate), Zwittergent 3-14, Octylglucoside, Digitonin, C12E8, Lubrol, Triton X-100, Nonidet P-40 and Tween 80. Properties of many common detergents are set forth below in Table 1.

The present invention encompasses methods for purifying polypeptides and complexes thereof in a sample that includes a detergent by reducing the detergent micelle concentration in the sample (e.g., to below the CMC) by chromatographic purification of the polypeptide or complex using a RAM of the present invention (e.g., as discussed herein).

TABLE 1

| Detergent properties | | | | |
|---|---|---|---|---|
| Detergent | Monomer, Da mw | Micelle, Da mw | CMC % (w/v) | CMC Molarity |
| Anionic | | | | |
| SDS | 288 | 18,000 | 0.23 | $8.0 \times 10^{-3}$ |
| Cholate | 430 | 4,300 | 0.60 | $1.4 \times 10^{-2}$ |
| Deoxycholate | 432 | 4,200 | 0.21 | $5.0 \times 10^{-3}$ |

TABLE 1-continued

Detergent properties

| Detergent | Monomer, Da mw | Micelle, Da mw | CMC % (w/v) | CMC Molarity |
|---|---|---|---|---|
| Cationic | | | | |
| C16TAB | 365 | 62,000 | 0.04 | $1 \times 10-3$ |
| Amphoteric | | | | |
| LysoPC | 495 | 92,000 | 0.0004 | $7 \times 10-6$ |
| CHAPS | 615 | 6,150 | 0.49 | $1.4 \times 10-3$ |
| Zwittergent 3-14 | 364 | 30,000 | 0.011 | $3.0 \times 10-4$ |
| Nonionic | | | | |
| Octylglucoside | 292 | 8,000 | 0.73 | $2.3 \times 10-2$ |
| Digitonin | 1,229 | 70,000 | — | — |
| C12E8 | 542 | 65,000 | 0.005 | $8.7 \times 10-5$ |
| Lubrol | 582 | 64,000 | 0.006 | $1.0 \times 10-4$ |
| Triton X-100 | 650 | 90,000 | 0.021 | $3.0 \times 10-4$ |
| Nonidet P-40 | 650 | 90,000 | 0.017 | $3.0 \times 10-4$ |
| Tween 80 | 1,310 | 76,000 | 0.002 | $1.2 \times 1015$ |

Restrictive Access Media (RAM)

"Restricted access media" or "restrictive access media" or "RAM" is a chromatographic media with dual properties: a) a sieving effect that excludes large molecules (like proteins) from interaction with the resin and b) adsorption of small molecules to the resin.

Figure 3:
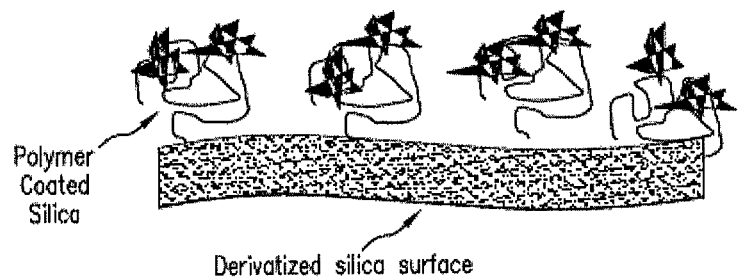
FIG. 3: Special Screening Media. Schematically shows drug screening media based on derivatized silica gel with two layers of coating. (1) Polymer, polysuccinamide with broad molecular weight distribution (5,000-700,000 Dalton) was bound to media particles (5µ, 60 A pores); (2) Hydrophilic compound (denaturalized HSA) is bound (immobilized) on the media particles outside the pores; (3) Hydrophilic compound (1-Ethyl propyl amine) is bound to the polymer inside "screen media" pores.

A RAM of the present invention is a derivatized gel, such as an aminopropyl silica gel, that is coated by polysuccinamide polymer with a broad molecular weight distribution from about 5,000 Daltons to about 700,000 Daltons to which (1) denatured human serum albumin (HSA) and (2) 1-ethylpropylamine is bound. The arrangement of a RAM of the present invention is as set forth in FIG. 3. In an embodiment of the invention, greater than 90% of the polysuccinamide polymer carbonyl groups are derivatized with human serum albumin and 1-ethylpropylamine (e.g., about 90%, about 91%, about 92%, about 93%, about 94%, about 95%, about 96%, about 97%, about 98%, about 99% or about 100%). In an embodiment of the invention, the polysuccinamide is attached to the support, via the aminopropyl groups, at several points per molecule and/or several points per support particle—this would be an "island" type of coating, as the individual polymer molecules are not cross-linked into a continuous network.

Generally, due to molecular size, the denatured HSA does not penetrate inside of the RAM pores due to size and, thus, is covalently attached to the polysuccinamide polymers on the outer surface of the support. In an embodiment of the invention, the denatured HSA is generally restricted to covalent attachment to polysuccinamide polymers on the outer surface of the support. The 1-ethylpropylamine molecules are not restricted from the pores and, thus, are largely located within the pore structure. In an embodiment of the invention, greater than 90% (e.g., about 90%, about 91%, about 92%, about 93%, about 94%, about 95%, about 96%, about 97%, about 98%, about 99% or about 100%) of the denatured HSA is located outside of the pores and greater than 90% (e.g., about 90%, about 91%, about 92%, about 93%, about 94%, about 95%, about 96%, about 97%, about 98%, about 99% or about 100%) of the 1-ethylpropylamine is located inside the pores.

In an embodiment of the invention, the pore size of a RAM of the present invention is about 60 angstroms and/or a RAM of the present invention bead size is about 5 microns in diameter.

In an embodiment of the invention, polysuccinamide polymers are attached to a support of a RAM of the present invention as set forth below:

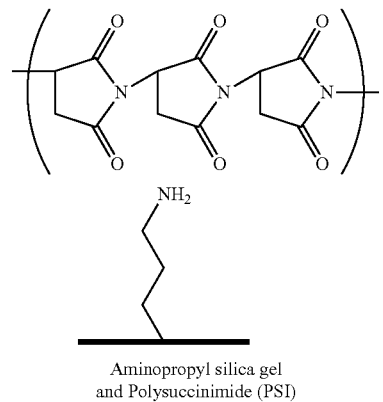

Aminopropyl silica gel and Polysuccinimide (PSI)

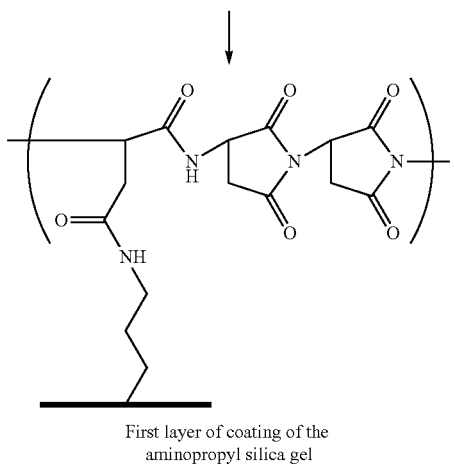

First layer of coating of the aminopropyl silica gel with polysuccinimide

Figure 1:
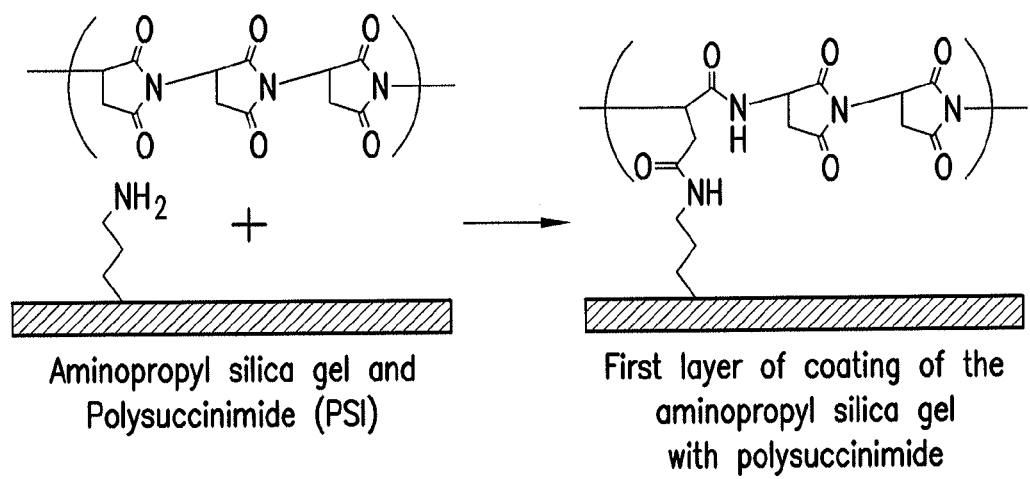
FIG. 1: Schematically shows obtaining the first level of coating of the aminopropyl silica gel by polysuccinamide (PSI).

See also FIG. 1. In an embodiment of the invention, succinamidyl units in a polysuccinamide polymer are derivatized with 1-ethylpropylamine as shown below:

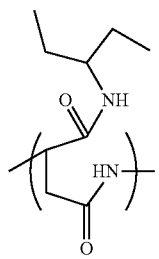

In an embodiment of the invention, the polysuccinamide polymers in the RAM of the present invention have a very broad molecular weight distribution, e.g., from about 10 angstroms in diameter to about 100 angstroms in diameter (e.g., about 10, 20, 30, 40, 50, 60, 70, 80, 90 or 100 angstroms).

In an embodiment of the invention, denatured human serum albumin is derivatized to the polysuccinamide by condensation between R—C(O)—R' of the polysuccinamide and R"-NH$_2$ of the polypeptide (e.g., at —NH$_2$ groups of glutamine, asparagine, lysine or arginine residues or at the amino terminus of the polypeptide); yielding RC(O)—NH—R"+H$_2$O.

Figure 2:
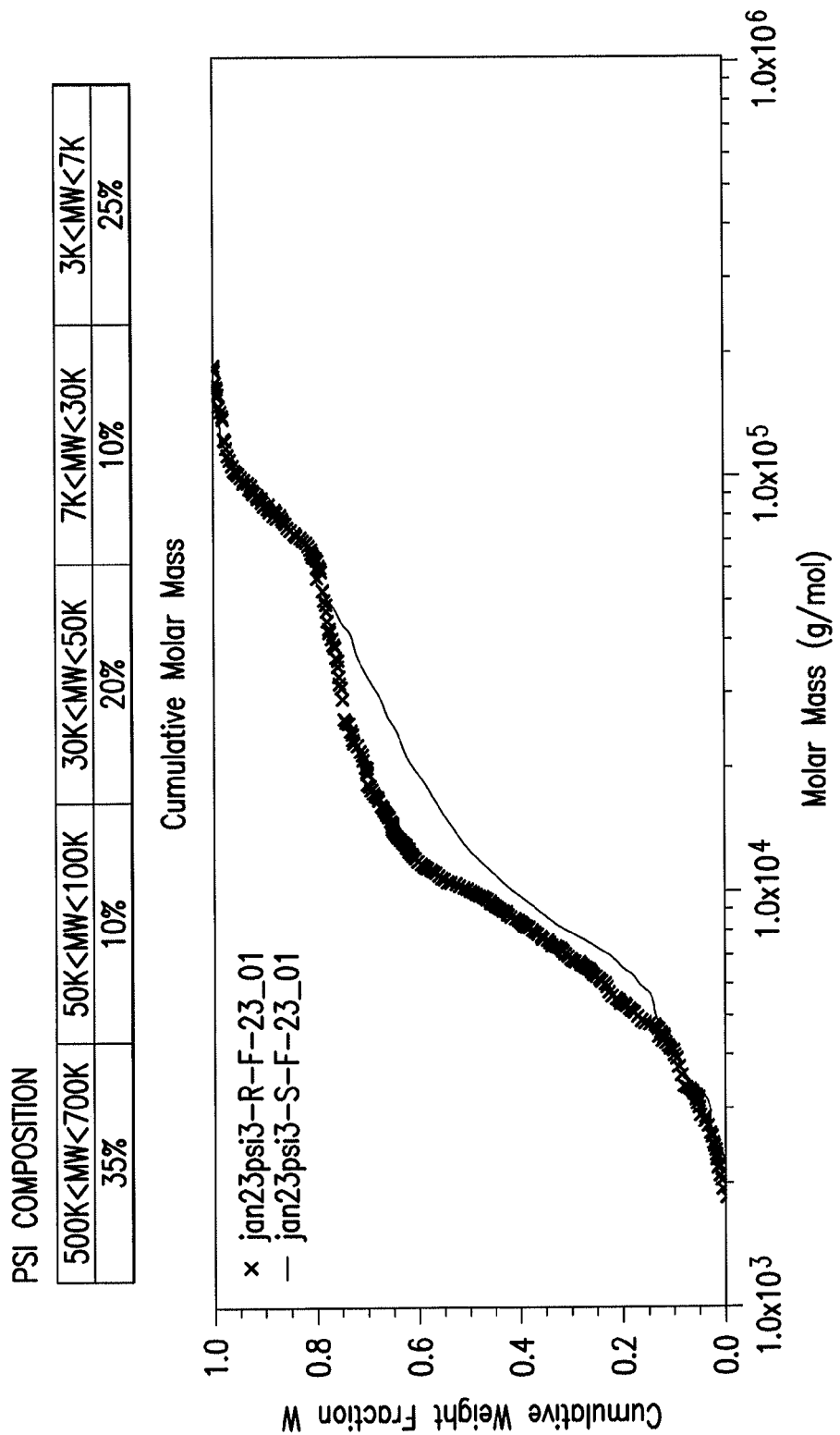
FIG. 2: Demonstrates the molecular weight distribution in the PSI used for the first layer of the coating.

In an embodiment of the invention, the molecular weight distribution of the derivatized polysuccinamide is approximately as set forth in the analysis set forth in FIG. 2. For example, comprising about 35% of the polymer in the range of about 500 kDa to about 700 kDa; about 10% of the polymer in the range of about 50 kDa to about 100 kDa; about 20% of the polymer in the range of about 30 kDa to about 50 kDa; about 10% of the polymer in the range of about 7 kDa to about 30 kDa; and about 25% of the polymer in the range of about 3 kDa to about 7 kDa.

Human serum albumin is very well known in the art and commercially available. For example, HSA has the following amino acid sequence:

(SEQ ID NO: 1)

```
MKWVTFISLL FLFSSAYSRG VFRR

DAHKSE VAHRFKDLGE ENFKALVLIA FAQYLQQCPF EDHVKLVNEV TEFAKTCVAD ESAENCDKSL

HTLFGDKLCT VATLRETYGE MADCCAKQEP ERNECFLQHK DDNPNLPRLV RPEVDVMCTA FHDNEETFLK

KYLYEIARRH PYFYAPELLF FAKRYKAAFT ECCQAADKAA CLLPKLDELR DEGKASSAKQ RLKCASLQKF

GERAFKAWAV ARLSQRFPKA EFAEVSKLVT DLTKVHTECC HGDLLECADD RADLAKYICE NQDSISSKLK

ECCEKPLLEK SHCIAEVEND EMPADLPSLA ADFVESKDVC KNYAEAKDVF LGMFLYEYAR RHPDYSVVLL

LRLAKTYETT LEKCCAAADP HECYAKVFDE FKPLVEEPQN LIKQNCELFE QLGEYKFQNA LLVRYTKKVP

QVSTPTLVEV SRNLGKVGSK CCKHPEAKRM PCAEDYLSVV LNQLCVLHEK TPVSDRVTKC CTESLVNRRP

CFSALEVDET YVPKEFNAET FTFHADICTL SEKERQIKKQ TALVELVKHK PKATKEQLKA VMDDFAAFVE

KCCKADDKET CFAEEGKKLV AASQAALGL
``` e.g., wherein residues 1-24 are signal peptide and the remaining residues are the mature HSA. Mature or immature denatured HSA can be used in a RAM of the present invention.

The "support" can be any material that can be derivatized as discussed herein and which is suitable for size-exclusion chromatographic purification (as discussed herein). In an embodiment of the invention, a support is an inorganic material. Inorganic support materials can include, but are not limited to, silica (e.g., a silica gel), glass, alumina, zirconia, silver, and gold. In an embodiment of the invention, a support is an organic support material. Organic support materials can include, but are not limited to, agarose, dextran, and cellulose. Supports can comprise one or more organic support material(s) and organic polymer supports. Organic support materials and organic polymer supports can include, but are not limited to, polystyrene, polymethacrylate, and polyamide. In other embodiments of the invention, the support can comprise a composite support. Composite supports include, but are not limited to, an agarose coating on quartz, an agarose coating on stainless steel, and coated polystyrene/divinylbenzene.

In an embodiment of the invention, the support must be a particle that has a diameter of about 5 microns and/or pores with a diameter of about 60 angstroms.

Purification

The RAM of the present invention is suitable for purifying a wide range of polypeptides and complexes thereof, for example, a target polypeptide and a small organic molecule ligand (e.g., a natural ligand, an antagonist or an agonist)

Typical methods by which a RAM of the present invention may be used to purify a preparation would include the steps of (i) introducing a sample containing a polypeptide or complex thereof to the RAM wherein the media is in a chromatography column.

A solvent in which the RAM is suspended can be, in an embodiment of the invention, alcohol (e.g., MeOH), water, aqueous buffer or an organic solvent at a pH of between about 1 and 8.

(ii) allowing the sample to pass over the RAM, e.g., under pressure.

The temperature can be up to about 60° C. (e.g., 4° C., 10° C., 23° C., 25° C., 37° C., 40° C., 50° C.) and the pressure under which a RAM column of the present invention is run can be up to about 9000 bar (e.g., about 1 bar, about 1000 bar, about 2000 bar, about 3000 bar, about 4000 bar, about 5000 bar, about 6000 bar, about 7000 bar, about 8000 bar);

(iii) collecting the flow-through fraction from the end of the column.

The flow-through faction and eluted fractions may then be analyzed and/or subject to further purification. For example, other purification steps can include cation exchange chromatography, anion exchange chromatography, further size exclusion chromatography, hydrophobic interaction chromatography, hydroxyapatite chromatography, diafiltration, ultrafiltration, precipitation (e.g., urea precipitation), viral filtration or filtration through a membrane, e.g., with pore size of 0.2 microns.

Low molecular weight and hydrophobic molecules tend to bind to the polymer inside the pores, and a high molecular weight and hydrophilic molecules tend to bind to the polymer outside the pores. The RAM of the present invention allows fast separation (e.g., about 10-20 sec) of small molecules (e.g., ligands with a molecular weight below about 1000 Dalton) from larger proteins.

A chromatography "column" is any vessel which can contain a RAM of the invention which permits the sample to pass through the RAM and, then out of the vessel. In an embodiment of the invention, the column is a generally cylindrical structure. The chromatography column can be, for example, metal (e.g., steel) or plastic. In general, the column must be capable of withstanding high pressure (e.g., 9000 bars). Column dimensions may be, in an embodiment of the invention, 2.1 mm×50 mm or 2.1 mm×33 mm (inner diameter X length).

Synthesis

The RAM of the present invention can be generated using any suitable means known in the art. In an embodiment of the invention, the RAM is generated by a method comprising:

(1) Derivatizing the support with polysuccinamide, for example by incubating the support, e.g., which comprises amino-propyl groups (e.g., silica gel), with polysuccinamide (e.g., 1%) in an organic solvent such as dimethylformamide (DMF), for example at a temperature of about 50° C. Afterward, the support can be washed, e.g., with the solvent (e.g., dimethylformamide) and with a mixture of the solvent (e.g., dimethylformamide) and water.

Loading of the amino-propyl groups in the RAM support must be at a rate of about 1.5-1.7 mmol polysuccinamide per gram of support.

A 1% polysuccinamide solution in DMF can be prepared by mixing the components in the correct proportions and then rotating the mixture for one day, and then filtering the mixture, e.g., using a "fine" grade of glass fritted funnel.

For example, in an embodiment of the invention, a 10% mixture of the support in a solution of 1% polysuccinamide in organic solvent (e.g., DMF) can be made and then incubated, e.g., with rotation e.g., for about 48 hours, e.g., at a temperature of about 50° C. After that, support can be washed, e.g., with the organic solvent (e.g., DMF), the a mixture of solvent: water::2:1 (e.g., DMF:$H_2O$::2:1). If the support is to be stored afterward, it may be kept moist with the solvent:$H_2O$ mixture. then (2) Binding denatured HSA to the polysuccinamide, for example, by incubating the support with a mixture of denaturing organic solvent (e.g., DMF) and denatured HSA, e.g., at about 50° C. Afterward, the support can be washed with a mixture of the solvent (e.g., DMF) and water and with water.

In an embodiment of the invention, a 5 mg/ml solution of HSA in water is initially prepared, e.g., at a temperature of about 50° C. After that, small portions (e.g., a few ml at a time) of a denaturing organic solvent such as DMF is added gradually e.g., at a temperature of about 50° C., with mixing. For example, about 1150 ml of the solvent (e.g., DMF) can be mixed into 500 ml of the HSA in water. In an embodiment of the invention, the HSA solution can be filtered before binding to the support. In an embodiment of the invention, about 50 grams of the support is mixed with the HSA mixture (e.g., about 1650 ml), e.g., with rotation for about 48 hours, e.g., at about 50° C. After coating, the resin can be washed, for example, with a solvent:water mixture (DMF:$H_2O$), then with $H_2O$ and then with solvent (e.g., DMF); e.g., all at about 50° C. then (3) Binding 1-ethylpropylamine to the HSA, for example, by incubating the gel with 1-ethyl propyl amine in organic solvent (e.g., DMF), e.g., at about 50° C., then washing the gel in the solvent (e.g., DMF), in water and in alcohol such as methanol;

In an embodiment of the invention, a 2/7 dilution of 1-ethylpropylamine is diluted with organic solvent such as DMF and the HSA coated support resin is added to this mixture; e.g., wherein 200 ml of the 1-ethylpropylamine is diluted with 500 ml of DMF and the 700 ml of solution is added to about 50 grams of the HSA coated support. The mixture may then be placed into vessel and rotated for e.g., about 36 hours, e.g., at about 50° C. The 1-ethylpropylamine coated resin may be was washed, e.g., with organic solvent, water, then alcohol, e.g., 1000 ml of solvent (e.g., DMF), 1000 ml of water and finally with 500 ml of MeOH.

The scope of the present invention encompasses any RAM produced by a method as set forth herein. Furthermore, the methods themselves that are discussed herein for making a RAM of the present invention are part of the present invention.

Screening Assays

The RAM of the present invention may be used to identify ligands that bind to a given target protein. For example, a mixture of the target and a mass encoded library may be equilibrated before adding to a size exclusion column containing the RAM of the present invention. As the mixture moves through the size exclusion column, ligand, target and target/ligand complexes separate; wherein, the complexes elute earlier than the ligand and target alone. The complexes are then, optionally, further fractionated, e.g., through a reverse phase chromatography column; wherein the complexes are further purified. In an embodiment of the invention, the ligand and the target protein are dissociated on the reverse phase chromatography column and the ligand is collected. The ligands are analyzed by mass spectrometry to determine their identity. A mass encoded library is a library comprising ligands whose molecular masses are known. Thus, the identity of a ligand in the library can be divined by determining its mass.

In an embodiment of the invention, the size exclusion column is about 2.1 mm in diameter and/or about 50 mm in length. In an embodiment of the invention, the buffer in which the size exclusion column is run is aqueous ammonium acetate buffer at a pH of about 7 to about 8; and/or at a concentration of about 700 mM to about 1 M. In an embodiment of the invention, the size exclusion column is run at about 0.4 ml per minute. In an embodiment of the invention, the size exclusion column is run at about 4° C.

In an embodiment of the invention, the reverse phase chromatography column is run with a buffer gradient of from about 100% water to about 100% of a mixture of acetonitrile and 0.2% formic acid. In an embodiment of the invention, the column pH is about 2 to about 3.

EXAMPLES

The present invention is intended to exemplify the present invention and not to be a limitation thereof. Any method or composition disclosed below falls within the scope of the present invention.

Example 1

Generation of the RAM and Column Packing Procedure

Preparation of PSI Solution.

One percent PSI in DMF was prepared, placed for rotation for one day, and then filtered using a "fine" grade of glass fritted funnel.

Preparation of Polysuccinamide Silica Gel. PSS. (First Layer of Coating)

The next day, 50 grams of the amino-propyl silica gel was added to the 500 ml solution of 1% PSI in DMF and placed into 2000 ml beaker with rotation for 48 hours at temperature 50° C. After that, the content of the bicker was washed with 1500 ml of DMF by means of using "fine" grade of glass fritted funnel. The next step was a similar washing of the PSS with 1500 ml of mixture DMF:$H_2O$::2:1. After the washing, the PSS was kept moist with the DMF:$H_2O$ mixture.

Preparation of HSA solution

Twenty five hundred mg of HSA was dissolved in 500 ml of water at 50° C. After that, small portions (a few ml) of DMF at temperature 50° C. were gradually added to the HSA solution with mixing. Finally, 1150 ml of the DMF was mixed with the 500 ml of the HSA in water.

Coating PSS with HSA (Second Layer of Coating Outside of Pore's Space)

The HSA solution was filtered with using glass-wool and placed together with 50 grams PSS into 2,000 ml bicker with rotation for 48 hours at 50° C. On the third day, the PSS coated with HSA was washed first with 3,000 ml of DMF:H₂0, then with 1,000 ml of H₂0 and finally with 500 ml of DMF. All liquids used for the washing had temperature 50° C.

Coating PSS with I-Ethyl Propyl Amine (Second Layer of Coating Inside of Pore's Space)

Two hundred ml of the 1-ethyl propyl amine was diluted with 500 ml of DMF and the 700 ml of solution was added to 50 grams PSS coated with HSA. The mixture was placed into 2,000 ml bicker and rotated for 36 hours at 50° C. After that, the coated PSS was washed with 1000 ml of DMF, then, 1000 ml of water and finally with 500 ml of MeOH.

Column Packing

The following procedure was used to pack the resulting media into a column:
1. Filled up container attached to a pump with isopropanol.
2. Installed on the pump pressure 8 000 psi.
3. Attached column to cartridge.
4. Weighed out 0.25 g of the coated PSS media and placed in a 20 ml vial.
5. Put 15 ml of isopropanol in the vial.
6. Vortexed the vial for 10 seconds and put it into sonicator for 10 minutes.
7. Put the contents of the vial into the cartridge.
8. Added hexane to the cartridge to fill up the cartridge.
9. Closed the cartridge completely and turned on the pump.
10. One hour later, turned off the pump.
11. Waited for 10-15 min while pressure reduced to zero and the solvent stopped dripping from the column.
12. Released the packed column from the cartridge.
13. Put waste containers under the cartridge.
14. Turn on the pump for 30 seconds to remove remaining media in the cartridge
15. Partially opened the cartridge to let remain liquid go out.

Figure 6:
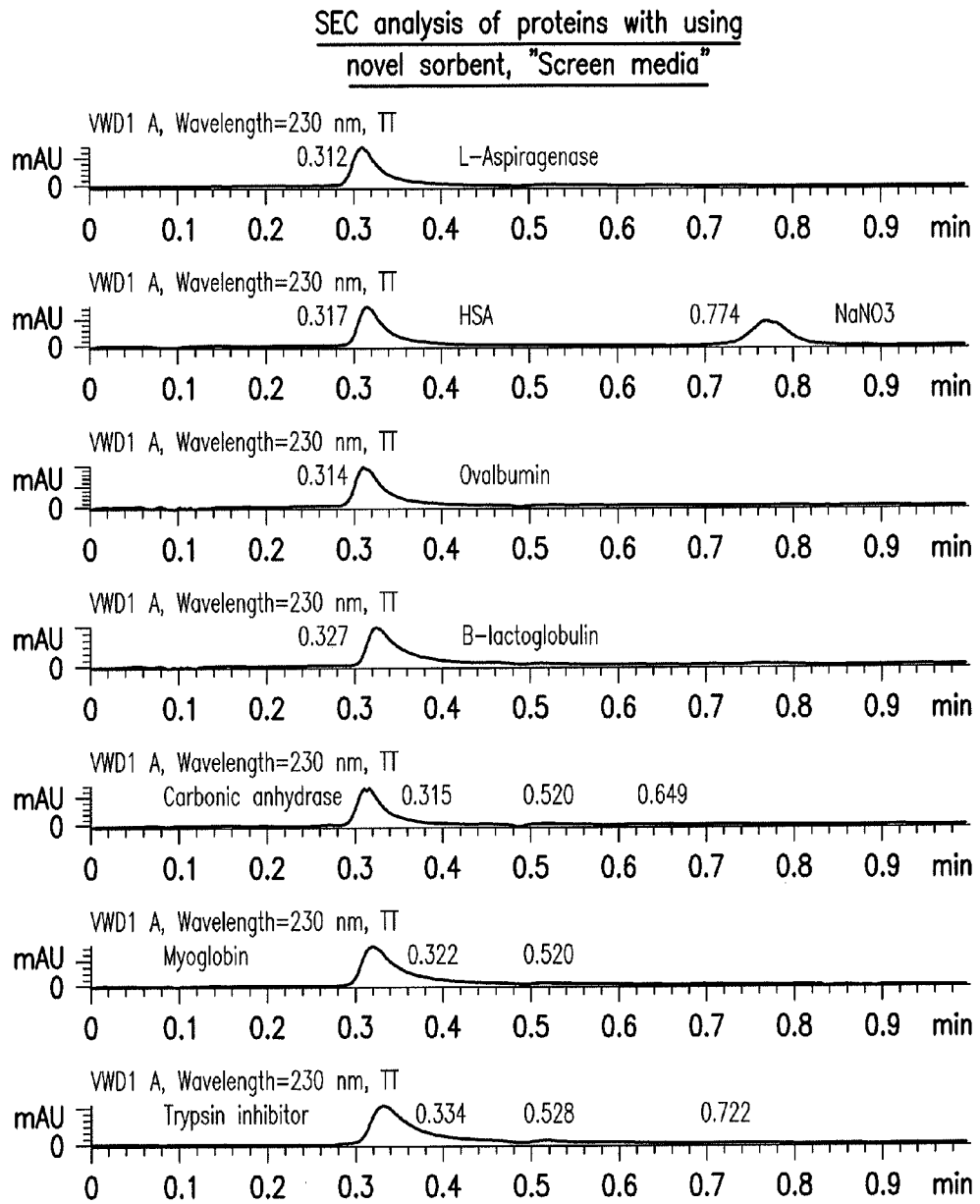
FIG. 6: Shows chromatograms of different proteins with molecular weight from 20,000 Dalton to 120,000 Dalton and the low molecular weight substance $NaNO_3$. The chromatograms were obtained on a column packed with the RAM of the present invention. This figure demonstrates that the large proteins cannot penetrate inside the RAM pores and therefore have retention volume equal to the void volume of the column. At the same time, the figure demonstrates perfect separation the low molecular weight substance, $NaNO_3$, from the proteins.
Figure 7:
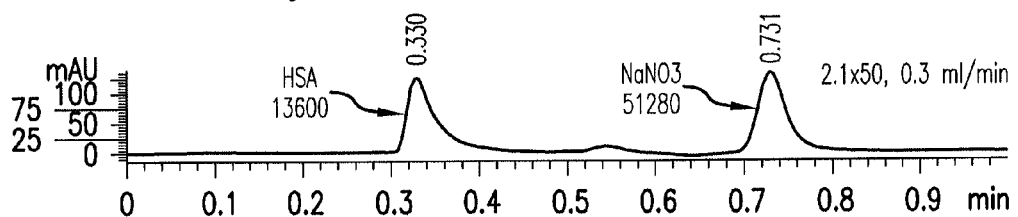
FIG. 7: Demonstrates separation of human serum albumin (HSA) from $NaNO_3$ on different size columns with an inner diameter of 2.1 mm and a length 50 or 33 mm, packed with the RAM of the present invention using flow rates of 0.3, 0.4 or 0.5 ml/min. The protein peak retention time was 19 seconds for the 50 mm column at a flow rate of 0.3 ml/min. A complete separation was achieved as well on the 33 mm column at a flow rate of 0.3, 0.4, or 0.5 ml/minute. At 0.5 ml/minute the protein retention time is just 9 seconds. Even at this rate and column length, the separation was complete.
Figure 7:
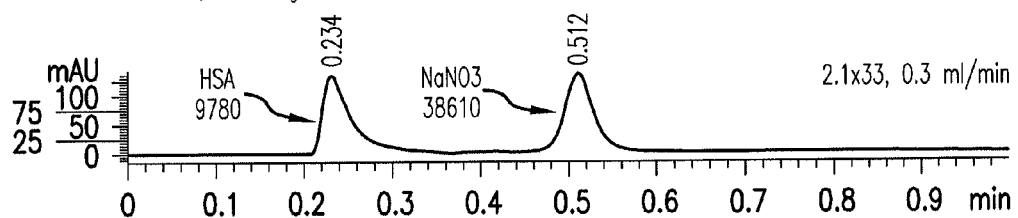
Figure 7:
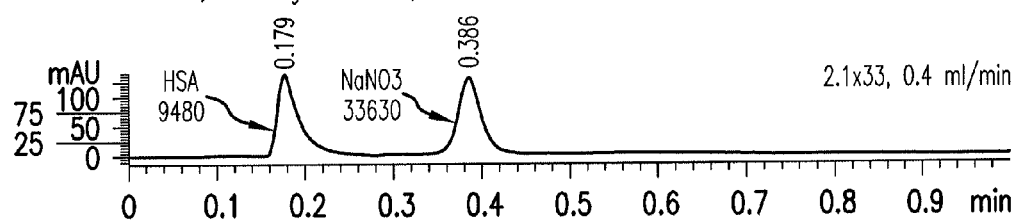
Figure 7:
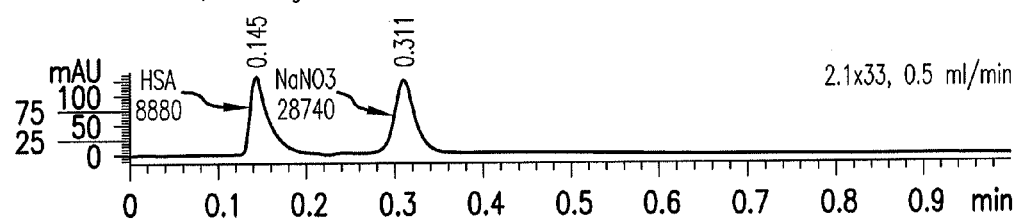
Figure 8:
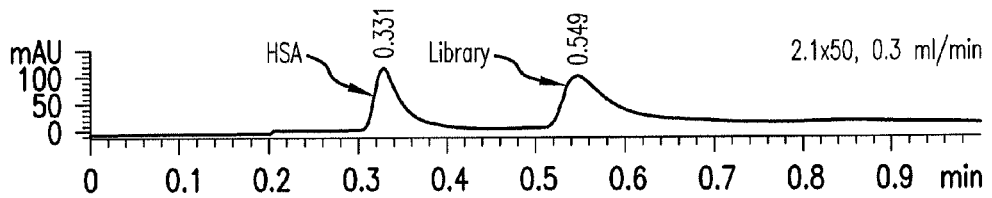
FIG. 8: Demonstrates separation of human serum albumin (HSA) from low molecular weight (MW) ligands in a library (containing 5,000 compounds of small molecules with MW below 800 Dalton). Different size columns are packed with the RAM of the present invention and used at different flow rates.
Figure 8:
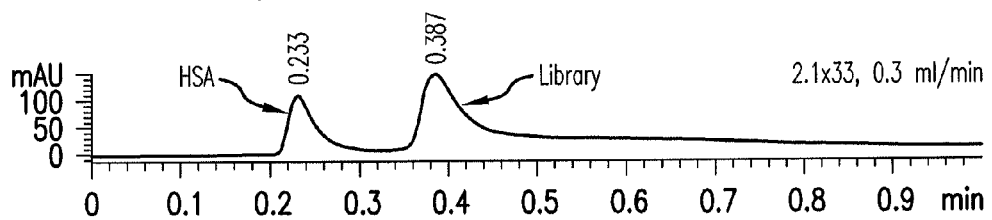
Figure 8:
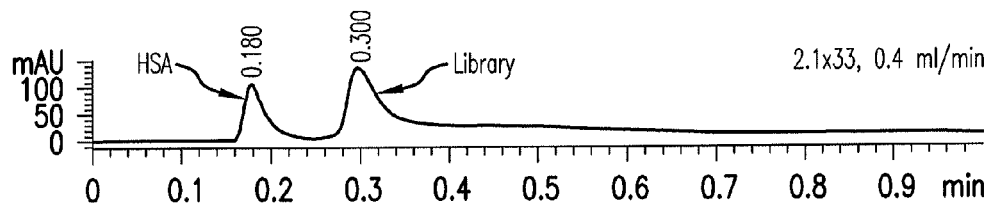
Figure 8:
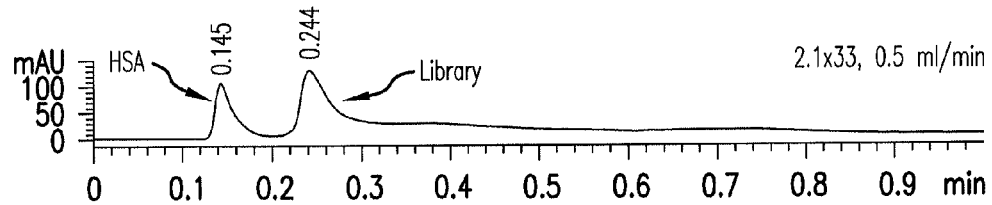

The size exclusion chromatograph obtained by separating human serum albumin from the smaller molecule NaNO₃ using the RAM of the present invention is set forth in FIG. 6. Separation of human serum albumin from NaNO₃ using various columns and flow rates resulted in chromatograms set forth in FIG. 7. Furthermore, a chromatogram demonstrating separation of human serum albumin from small molecules in a library using various flow rates and column sizes is set forth in FIG. 8.

The present invention is not to be limited in scope by the specific embodiments described herein. Indeed, the scope of the present invention includes embodiments specifically set forth herein and other embodiments not specifically set forth herein; the embodiments specifically set forth herein are not necessarily intended to be exhaustive. Various modifications of the invention in addition to those described herein will become apparent to those skilled in the art from the foregoing description. Such modifications are intended to fall within the scope of the claims.

Patents, patent applications, publications, product descriptions, and protocols are cited throughout this application, the disclosures of which are incorporated herein by reference in their entireties for all purposes.

We claim:

1. A particle comprising a diameter of about 5 microns and a support comprising a surface that comprises pores of about 60 angstroms in diameter; wherein the surface of the support is coated with aminopropyl groups that are derivatized with polysuccinimide polymers which polymers are derivatized with 1-ethylpropylamine and with denatured human serum albumin wherein greater than 90% of the 1-ethylpropylamine is located within the particle pores and greater than 90% of the denatured human serum albumin is located outside the particle pores.

2. The particle of claim 1 where the support is silica.

3. A particle comprising a diameter of about 5 microns comprising a support that comprises a surface comprising pores of about 60 angstroms in diameter, wherein the surface of the support is coated with aminopropyl groups that are derivatized with polysuccinimide polymers which polymers are derivatized with 1-ethylpropylamine and with denatured human serum albumin wherein greater than 90% of the 1-ethylpropylamine is located within the particle pores and greater than 90% of the denatured human serum albumin is located outside the particle pores, that is produced by a process comprising:
  (1) incubating a particle comprising aminopropyl groups with 1% polysuccinimide in dimethylformamide under conditions whereby said aminopropyl groups are derivatized with polysuccinimide;
  (2) incubating the particle with denatured human serum albumin under conditions whereby the polysuccinimide is derivatized with denatured human serum albumin; and
  (3) incubating the particle with 1-ethylpropylamine under conditions whereby the polysuccinimide is derivatized with 1-ethylpropylamine.

4. The particle of claim 3 where said particle comprising aminopropyl groups is a silica gel particle comprising aminopropyl groups.

5. The particle of claim 3 produced by a process comprising:
  (1) incubating a particle comprising a support that comprises a surface that comprises pores comprising aminopropyl groups with 1% polysuccinimide in dimethylformamide at about 50° C.; and then washing the particle to remove excess polysuccinimide; then
  (2) incubating the particle with a mixture of dimethylformamide and denatured human serum albumin at about 50° C.; and then washing the particle to remove excess denatured human serum albumin; then
  (3) incubating the particle with 1-ethylpropyl amine in dimethylformamide at about 50° C., then washing the particle to remove excess 1-ethylpropylamine; wherein said particle has a diameter of about 5 microns and pores with a diameter of about 60 angstroms.

6. The particle of claim 5 wherein said particle comprising aminopropyl groups is a silica gel particle comprising aminopropyl groups.

7. The particle of claim 1 wherein about 100% of said aminopropyl groups are derivatized with polysuccinimide; and about 100% of said polysuccinimidyl groups are derivatized with denatured human serum albumin and 1-ethylpropylamine.

8. The particle of claim 5 wherein the wash in step (1) comprises washing with particle with dimethylformamide and with a mixture of dimethylformamide and water; the wash in step (2) comprises washing with particle with a mixture of dimethylformamide and water and with water; and the wash in step (3) comprises washing with particle with dimethylformamide, with water and with methanol.

9. A method for dispersing detergent micelles from a sample comprising a polypeptide; comprising adding the sample to a column comprising particles of claim 1, allowing the sample to fractionate in the column, and collecting eluate comprising the polypeptide from the column.

10. The method of claim 9 further comprising purifying said polypeptide by size exclusion chromatography, anion exchange chromatography, cation exchange chromatography, hydrophobic interaction chromatography, hydroxyapatite chromatography, filtration, diafiltration, ultrafiltration, precipitation or viral filtration.

11. The method of claim 9 wherein the detergent is sodium dodecyl sulfate, Cholate, Deoxycholate, C16TAB, LysoPC, CHAPS, Zwittergent 3-14, Octylglucoside, Digitonin, C12E8, Lubrol, Triton X-100, Nonidet P-40 or Tween 80.

12. A method for making the particle of claim 1 comprising:
  (1) incubating a particle comprising aminopropyl groups with 1% polysuccinimide in dimethylformamide;
  (2) incubating the particle with denatured human serum albumin; and
  (3) incubating the particle with 1-ethylpropylamine.

13. The method of claim 12 where said support particle comprising aminopropyl groups is a silica gel particle comprising aminopropyl groups.

14. The method of claim 12 comprising: (1) incubating a support particle comprising aminopropyl groups with 1% polysuccinimide in dimethylformamide at about 50° C.; and then washing the particle to remove excess polysuccinimide; then (2) incubating the particle with a mixture of dimethylformamide and denatured human serum albumin at about 50° C.; and then washing the particle to remove excess denatured human serum albumin; then (3) incubating the particle with 1-ethylpropyl amine in dimethylformamide at about 50° C., then washing the particle to remove excess 1-ethylpropylamine; wherein said particle has a diameter of about 5 microns and pores with a diameter of about 60 angstroms.

15. The method of claim 14 wherein the wash in step (1) comprises washing with particle with dimethylformamide and a with mixture of dimethylformamide and water; the wash in step (2) comprises washing with particle with a mixture of dimethylformamide and water and with water; and the wash in step (3) comprises washing with particle with dimethylformamide, with water and with methanol.

* * * * *

SEQUENCE LISTING

```
<160> NUMBER OF SEQ ID NOS: 1

<210> SEQ ID NO 1
<211> LENGTH: 609
<212> TYPE: PRT
<213> ORGANISM: Homo sapiens
<220> FEATURE:
<221> NAME/KEY: SIGNAL
<222> LOCATION: (1)..(24)

<400> SEQUENCE: 1

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160
```

```
Lys Tyr Leu Tyr Glu Ile Ala Arg Arg His Pro Tyr Phe Tyr Ala Pro
                165                 170                 175
Glu Leu Leu Phe Phe Ala Lys Arg Tyr Lys Ala Ala Phe Thr Glu Cys
                180                 185                 190
Cys Gln Ala Ala Asp Lys Ala Ala Cys Leu Leu Pro Lys Leu Asp Glu
                195                 200                 205
Leu Arg Asp Glu Gly Lys Ala Ser Ser Ala Lys Gln Arg Leu Lys Cys
            210                 215                 220
Ala Ser Leu Gln Lys Phe Gly Glu Arg Ala Phe Lys Ala Trp Ala Val
225                 230                 235                 240
Ala Arg Leu Ser Gln Arg Phe Pro Lys Ala Glu Phe Ala Glu Val Ser
                245                 250                 255
Lys Leu Val Thr Asp Leu Thr Lys Val His Thr Glu Cys Cys His Gly
                260                 265                 270
Asp Leu Leu Glu Cys Ala Asp Asp Arg Ala Asp Leu Ala Lys Tyr Ile
                275                 280                 285
Cys Glu Asn Gln Asp Ser Ile Ser Ser Lys Leu Lys Glu Cys Cys Glu
            290                 295                 300
Lys Pro Leu Leu Glu Lys Ser His Cys Ile Ala Glu Val Glu Asn Asp
305                 310                 315                 320
Glu Met Pro Ala Asp Leu Pro Ser Leu Ala Ala Asp Phe Val Glu Ser
                325                 330                 335
Lys Asp Val Cys Lys Asn Tyr Ala Glu Ala Lys Asp Val Phe Leu Gly
                340                 345                 350
Met Phe Leu Tyr Glu Tyr Ala Arg Arg His Pro Asp Tyr Ser Val Val
                355                 360                 365
Leu Leu Leu Arg Leu Ala Lys Thr Tyr Glu Thr Thr Leu Glu Lys Cys
            370                 375                 380
Cys Ala Ala Ala Asp Pro His Glu Cys Tyr Ala Lys Val Phe Asp Glu
385                 390                 395                 400
Phe Lys Pro Leu Val Glu Glu Pro Gln Asn Leu Ile Lys Gln Asn Cys
                405                 410                 415
Glu Leu Phe Glu Gln Leu Gly Glu Tyr Lys Phe Gln Asn Ala Leu Leu
                420                 425                 430
Val Arg Tyr Thr Lys Lys Val Pro Gln Val Ser Thr Pro Thr Leu Val
            435                 440                 445
Glu Val Ser Arg Asn Leu Gly Lys Val Gly Ser Lys Cys Cys Lys His
450                 455                 460
Pro Glu Ala Lys Arg Met Pro Cys Ala Glu Asp Tyr Leu Ser Val Val
465                 470                 475                 480
Leu Asn Gln Leu Cys Val Leu His Glu Lys Thr Pro Val Ser Asp Arg
                485                 490                 495
Val Thr Lys Cys Cys Thr Glu Ser Leu Val Asn Arg Arg Pro Cys Phe
                500                 505                 510
Ser Ala Leu Glu Val Asp Glu Thr Tyr Val Pro Lys Glu Phe Asn Ala
            515                 520                 525
Glu Thr Phe Thr Phe His Ala Asp Ile Cys Thr Leu Ser Glu Lys Glu
            530                 535                 540
Arg Gln Ile Lys Lys Gln Thr Ala Leu Val Glu Leu Val Lys His Lys
545                 550                 555                 560
Pro Lys Ala Thr Lys Glu Gln Leu Lys Ala Val Met Asp Asp Phe Ala
                565                 570                 575
```

```
                                        -continued

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu
```